(12) United States Patent
Perraut et al.

(10) Patent No.: US 8,749,792 B2
(45) Date of Patent: Jun. 10, 2014

(54) DEVICE FOR OPTICAL MEASUREMENT OF MATERIALS, USING MULTIPLEXING OF LIGHT

(75) Inventors: Francois Perraut, Saint Joseph de Riviere (FR); Henri Grateau, Le Gua (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 0 days.

(21) Appl. No.: 13/596,485

(22) Filed: Aug. 28, 2012

(65) Prior Publication Data

US 2013/0057867 A1 Mar. 7, 2013

(30) Foreign Application Priority Data

Sep. 2, 2011 (FR) ...................................... 11 57810

(51) Int. Cl.
*G01N 21/55* (2014.01)
(52) U.S. Cl.
USPC ..................... 356/446; 250/208.1; 250/214.1; 356/445; 356/213
(58) Field of Classification Search
USPC ..................... 250/208.1, 214.1; 356/213, 445
See application file for complete search history.

(56) References Cited

U.S. PATENT DOCUMENTS

| | | | |
|---|---|---|---|
| 5,779,978 A | 7/1998 | Hartmann et al. | |
| 6,614,215 B1 | 9/2003 | Wood | |
| 7,064,893 B2 | 6/2006 | Boutet et al. | |
| 7,396,650 B2 * | 7/2008 | Perraut et al. | ............. 435/7.1 |
| 7,911,700 B2 | 3/2011 | Chao et al. | |
| 8,173,440 B2 | 5/2012 | Paolacci et al. | |
| 2004/0008393 A1 | 1/2004 | Matsushita et al. | |
| 2004/0252943 A1 | 12/2004 | Schilling | |
| 2006/0289787 A1 | 12/2006 | Ohman et al. | |
| 2009/0091837 A1 | 4/2009 | Chao et al. | |
| 2012/0113421 A1 | 5/2012 | Vignoud et al. | |

FOREIGN PATENT DOCUMENTS

| | | |
|---|---|---|
| EP | 2 423 668 A1 | 2/2012 |
| WO | WO 2004/055502 A2 | 7/2004 |
| WO | WO 2004/055502 A3 | 7/2004 |
| WO | WO 2006/135306 A1 | 12/2006 |
| WO | WO 2007/031657 A2 | 3/2007 |

OTHER PUBLICATIONS

U.S. Appl. No. 13/591,524, filed Aug. 22, 2012, Perraut et al.

(Continued)

*Primary Examiner* — Michael A Lyons
*Assistant Examiner* — Iyabo S Alli
(74) *Attorney, Agent, or Firm* — Oblon, Spivak, McClelland, Maier & Neustadt, L.L.P.

(57) ABSTRACT

A device for optical measurement of materials includes a zone opposite a dot including a material, a light source emitting light along an axis in the direction of the zone, where the material interacts with the light it receives, and a light guide to convey a proportion of the light emitted by the dot under the effect of the illumination. The guide includes a light scatterer associated with the source and causing a proportion of the light emitted by the dot to penetrate into the guide, such that it is guided in a direction perpendicular to the axis; the scatterer is annular in shape, and thus delimits a zone of the light guide, and the area of the zone is greater than or equal to the area of the cross-section of the portion of light beam incident to the material.

12 Claims, 8 Drawing Sheets

(56) References Cited

OTHER PUBLICATIONS

Search Report issued Mar. 30, 2012 in French Application No. 1157810 (With English Translation of Category of Cited Documents).

E. Schultz, et al., "A novel fluorescence-based array biosensor: Principle and application to DNA hybridization assays", Biosensors and Bioelectronics, vol. 23, 2008, pp. 987-994.

Romain Dagnelie, et al., "Méthodes de Mesure du Formaldéhyde dans L'Atmosphère", Revue Air Pur No. 74, Premier Semestre, 2008, pp. 14-21.

J. M. Elson, et al., "Relationship of the total integrated scattering from multiplayer-coated optics to angle of incidence, polarization, correlation length, and roughness cross-correlation properties", Applied Optics, vol. 22, No. 20, Oct. 15, 1983, pp. 3207-3219.

Edina Németh, et al., "Real-time study of the effect of different stress factors on lactic acid bacteria by electrochemical optical waveguide lightmode spectroscopy", Biomolecular Engineering, vol. 24, 2007, pp. 631-637.

Yuan-Yu Lin, et al., "Integration of polymer light-emitting diode and polymer waveguide on Si substrate", Applied Physics Letters, vol. 89, 2006, pp. 063501-1 to 063501-3.

\* cited by examiner

DEVICE FOR OPTICAL MEASUREMENT OF MATERIALS, USING MULTIPLEXING OF LIGHT

TECHNICAL FIELD

The present invention relates to a device for optical measurement of materials, using multiplexing of light.

It applies notably to the optical measurement of liquid or gaseous samples, which may contain analytes, i.e. molecules, or determined chemical or biological sequences, or again microorganisms, in which there is interest.

In the invention use is made of multiplexing of light. Indeed, the same optical detector, or photodetector, is used to measure samples which are placed in separate zones.

The optical measurements, made by means of the invention, can notably be measurements of transmission or absorption, measurements of diffusion, or measurements of photoluminescence, for thin or thick layers of liquids or gases.

STATE OF THE PRIOR ART

Various devices for optical measurement of samples using multiplexing of light are already known.

Some known devices use a relative displacement of the samples, using mechanical means, relative to an assembly including a light source and a photodetector. And with these devices, the respective optical responses of the samples are measured sequentially.

In other known devices a light source simultaneously illuminates all the samples. Each of the latter is associated with a first end of an optical fibre which receives the light originating from the sample.

Both ends of the assembly of optical fibres used in this fashion are connected in succession to an additional optical fibre which is displaced by mechanical means with a view to these successive connections. This additional optical fibre transmits the light which it receives in succession to a given photodetector.

In other known devices a light source also simultaneously illuminates all the samples. An appropriate optical system projects the images of the samples on to a photodetector consisting of a matrix of photosites. As a variant, it has a single photosite and a matrix with programmable transparency is positioned between the samples and the photosite.

Another device is known by the following document [1] to which reference will be made:
E. Schultz et al., Biosensors and Bioelectronics, Vol. 23 (2008), pages 987 to 994.

In this other known device optical sources are respectively placed in front of the samples and are illuminated sequentially. The light originating respectively from the samples is captured by a glass plate the faces of which are polished. The measurement is made using a photodetector, in synchrony with the illumination sequence.

The light-glass plate coupling occurs only for certain interactions of the light with the samples, for example an interaction of the fluorescence type. In addition the samples must be thin: they must be thinner than the emission wavelength of the fluorescent compounds constituting the samples or included in them. In this case the light penetrates naturally into the plate by evanescent coupling, or near-field coupling.

With this type of coupling the quantity of light which penetrates into the plate decreases exponentially with the distance from the fluorophores to the surface of the plate. As a consequence, the device known by document [1] is unsuitable for analysis of samples consisting of thick layers.

More specifically, if the thickness of an analysed sample is greater than $10\lambda$, where $\lambda$ is the wavelength of the fluorescence light, the light energy which penetrates into the plate becomes very small and is difficult to detect.

This known device is therefore unsuitable for measurements of transmission, diffusion or fluorescence, made on thick samples, which can be gaseous, liquid, solid, or in the form of powders.

Indeed, in the case of transmission measurements, a sample has no source to re-emit the light: the light is absorbed, or not absorbed, by the sample, and only the fraction of light which has not interacted with this sample is measured.

In the case of measurements of diffusing samples, it may be considered that the light is re-emitted by the molecules that the sample comprises and constituting secondary sources; but only those which are present in a layer having a low thickness contribute to producing a measurable signal. The latter is then very small relative to the total signal.

In fact, it should be noted that when an analyte penetrates in a thick layer over a small thickness the light is diffused far from the surface of the glass plate, such that evanescent coupling cannot occur.

The same reasoning is applicable to thick fluorescent samples: only fluorophores the distance of which to the surface of the glass plate is less than $10\lambda$, where $\lambda$ is the wavelength of the fluorescence light, contribute to providing a measurable signal.

DESCRIPTION OF THE INVENTION

The aim of the present invention is to remedy the above disadvantages.

It enables optical measurements to be made on dots, including sensor materials which absorb or diffuse the light, or which are fluorescent samples, and which can be thicker than the wavelength of the detected radiation.

To accomplish this the present invention uses a forced coupling of the light used for measurement, using appropriate couplers.

In precise terms, the object of the present invention is a device for optical measurement of a material, including:
  a transparent support, including at least one zone, where this zone is intended to be positioned opposite a dot including a material,
  a light source associated with the said zone, where the light source is designed to emit light along an axis, in the direction of the zone with which it is associated, where the material that the dot has interacts with the light it receives from the said light source, and
  a light guide to convey a proportion of the light emitted by the dot, under the effect of illumination by the light source,
  characterised in that the light guide includes a light scatterer associated with the said light source, where the said scatterer can cause a proportion of the light emitted by the dot to penetrate into the said light guide, such that it is guided in a direction perpendicular to the axis of the light emitted by the said light source.

According to a preferred embodiment of the invention, the light guide is multi-mode.

The device forming the object of the invention can have multiple dots.

According to a particular embodiment of the invention, the device also includes a photodetector to detect the light conveyed by the light guide, where this photodetector is positioned opposite the edge of the light guide.

According to a preferred embodiment of the device forming the object of the invention, the light guide's thickness is in a range of 50 µm to 10 mm, and preferably of 500 µm to 5 mm.

The scatterer is advantageously positioned, at least partly, on the face of the light guide closest to the material.

According to a particular embodiment of the device forming the object of the invention, the source emits, in the direction of the material, light in the form of a light beam, where the area of a scatterer is then less than or equal to the area of the cross-section of the portion of the light beam incident to the material.

According to another particular embodiment, the scatterer is annular in shape, and thus delimits a zone of the light guide, and the area of the zone is greater than or equal to the area of the cross-section of the portion of the light beam incident to the material.

According to a particular embodiment of the invention, the scatterer is in two portions which are of equal size, and which are located respectively on two opposite faces of the light guide.

According to a particular embodiment of the invention, the scatterer is in two portions which are of different size, and which are located respectively on two opposite faces of the light guide.

The scatterer is preferably constituted by a rough surface zone of the light guide, the arithmetical roughness of which is in a range of 100 nm to 50 µm. This enables elastic scattering of light to be favoured over the diffraction phenomenon. In other words, with such roughness, the deflection of the light in the guide occurs principally by elastic scattering. This is a simpler solution than the use of diffraction grating. Thus, the term "scatterer" is understood to mean an element able to deflect a light which it receives by scattering.

According to a particular embodiment of the invention, the light guide constitutes the transparent support and thus includes the zone intended to receive the contact, where this zone is positioned opposite the scatterer.

According to a particular embodiment, the device forming the object of the invention includes a main light source and at least one optical element of variable transparency which is able to receive the light from the main light source and then to constitute the light source.

According to one embodiment the device includes a plurality of materials, intended to be illuminated, preferably in succession, by a source.

Each material then has a scatterer associated with it which enables the light emitted by the dot or, more specifically, the material included in the dot, to be deflected in the lightguide, under the effect of the illumination by the source.

A material can be a sensor material, i.e. a material the optical properties of which change when it is placed in contact with an analyte.

The device forming the object of the invention can include a plurality of materials and in addition a set of pits which are intended respectively to receive the materials, where each pit is positioned respectively opposite a scatterer.

BRIEF DESCRIPTION OF THE DRAWINGS

The present invention will be better understood on reading the description of example embodiments given below, purely as an indication and in no sense restrictively, making reference to the appended illustrations in which.

DETAILED ACCOUNT OF PARTICULAR EMBODIMENTS

Figure 1A:
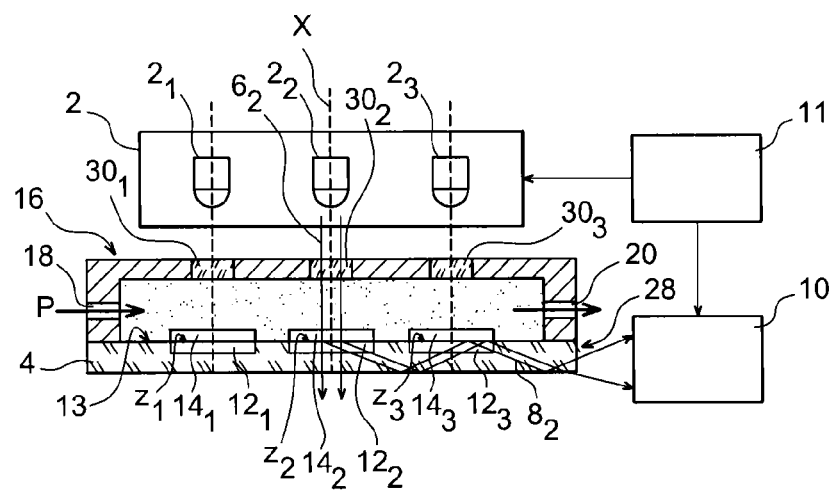
FIG. 1A is a schematic section view of a first particular embodiment of the device forming the object of the invention, which uses several light sources, and in which the dots and coupling elements are on the same plate.

FIG. 1A is a schematic section view of a particular embodiment of the optical measurement device forming the object of the invention.

The device represented schematically in FIG. 1A is intended to measure dots optically. It includes an assembly 2 of light sources. Only light sources $2_1$, $2_2$, $2_3$ are represented in FIG. 1A.

The device of FIG. 1A also includes a transparent support 4, including zones, called "interrogation zones", which are intended to receive the dots respectively. The light sources are respectively associated with these zones.

Each light source is provided to emit a light beam in the direction of the zone associated with it. Only light beam $6_2$, emitted by source $2_2$, is represented in FIG. 1A and the axis of this light beam is referenced X.

Each dot interacts with the light it receives from the light source corresponding to it.

A dot generally includes a material, and notably a sensor material, the optical properties of which may change when it is brought into contact with an analyte.

Thus, when a fluid, for example a gas or liquid, flows in contact with the dot, and when the fluid contains an analyte to which the sensor material is sensitive, the dot, due to the sensor material it contains, undergoes a modification of its optical properties.

"Modification of the optical properties" is understood to mean an emission of a fluorescence light, a change of colour, or a modification of absorption.

The device of FIG. 1A also includes a light guide to convey a portion of the light beam resulting from the interaction of each dot with the light which it has received.

For example, in FIG. 1A light $8_2$ conveyed by the light guide can be seen, following the interaction of a dot with light beam $6_2$.

In the example represented in FIG. 1A the light guide constitutes transparent support 4 and thus includes the zones, such as zones $z_1$, $z_2$, $z_3$, intended to receive the dots respectively.

The device of FIG. 1A also includes:
- a photodetector 10 to detect a proportion of the light conveyed by light guide 4, and
- means 11 for controlling the light sources, in order to illuminate and then turn off the sources one after another, so as to detect in succession the lights corresponding respectively to the different dots, and therefore to read the support with the various interrogation zones.

Control means 11 are preferably provided such that they illuminate and then turn off the light sources sequentially, synchronising the illumination-extinction of each source with the measurement of the corresponding light, made by photodetector 10.

The light sources can be chosen from among light-emitting diodes, connected optical fibres, or laser diodes.

Light guide 4 is usually a multi-mode light guide. It includes an assembly of coupling elements, which are respectively associated with the light sources, and constitute light scatterers.

Each light scatterer is able to cause a portion of the light beam resulting from the interaction of the corresponding dot with the light which it has received to penetrate into multimode light guide 4.

The various interrogation zones are positioned respectively facing the scatterers. Among the latter, only scatterers $12_1$, $12_2$, $12_3$, corresponding respectively to sources $2_1$, $2_2$, $2_3$, are represented in FIG. 1A.

In the example of FIG. 1A, multi-mode light guide 4 is a plate with parallel faces, made for example of glass, silica, quartz or plastic, which is between 50 μm and 10 mm thick, and preferably between 500 μm and 5 mm thick. One of the plate's two faces, namely face 13, is positioned facing assembly 2 of light sources and in contact with sensor dots $14_1$, $14_2$ and $14_3$. The assembly of scatterers is formed at this face 13.

In addition, the device of FIG. 1A uses an assembly of dots which are sensitive to analytes, where the latter may be biological or chemical compounds. These dots, which can contain different sensor materials, which are sensitive to different analytes, are positioned respectively on the interrogation zones which are located on face 13, respectively above the scatterers. Only contacts $14_1$, $14_2$, $14_3$ are represented in FIG. 1A.

As previously described, exposing these dots to the biological or chemical compounds modifies their optical properties. This modification causes the quantity of light transmitted, or the quantity of light scattered, or again the fluorescence of these dots, to vary. These variations can be positive or negative.

These dots are exposed to a portion P of a fluid (liquid or gas), which may contain the compounds, or analytes, which it is desired to detect or to dose. To accomplish this, plate 4 may possibly be positioned in a circulation chamber 16 which is fitted with an aperture 18, designed to allow this portion P of fluid to enter the chamber, and another aperture 20, designed to allow portion P of fluid to leave the chamber.

In the example of FIG. 1A, each sample consists of a sensitive material which is exposed to the fluid.

Each light source is associated with a single scatterer, and the pair constituted by the latter and the corresponding light source is itself associated with a single dot, positioned on the interrogation zone opposite the associated light source.

As an example, source $2_2$ is associated with scatterer $12_2$ and with dot $14_2$.

In the case of FIG. 1A, only light source $2_2$ is illuminated, and the corresponding interrogation zone, supporting dot $14_2$, is interrogated.

The sensor materials can be porous polymers or sol-gels, for example as described in application WO 2007/031657 and in the article of R. Dagnelie et al., "Méthodes de mesure du formaldehyde dans l'atmosphère", Revue Air Pur N° 74, pages 14-21.

It will be noted that the more the dot including the sensor material is volume-based and not surface-based the greater the invention's applicability.

Figure 1B:
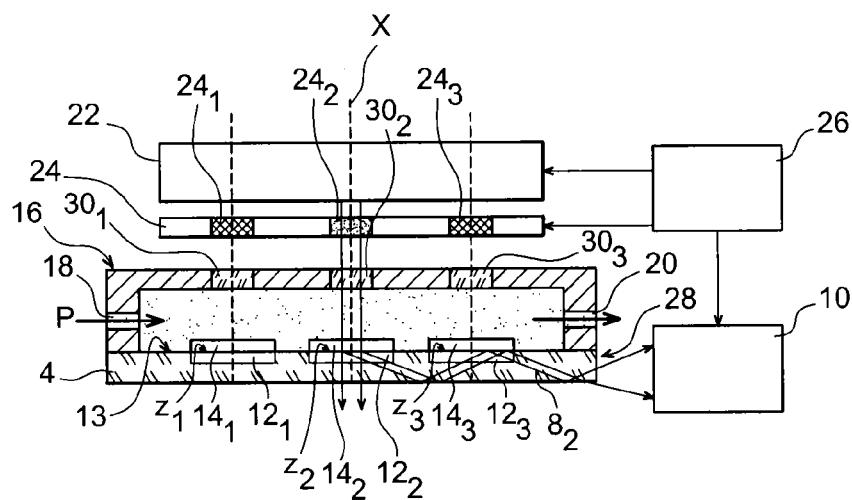
FIG. 1B is a schematic section view of another particular embodiment, which uses a single light source and a variable-transparency matrix.

In another particular embodiment of the invention, illustrated schematically by FIG. 1B, a single light source 22 is used which is able to illuminate the entire face 13 of plate 4 which supports the dots.

A variable-transparency matrix 24, including an assembly of variable-transparency optical elements, is inserted between source 22 and the assembly of interrogation zones. Only elements $24_1$, $24_2$, $24_3$, are represented in FIG. 1B. On this subject, reference will be made to the following document:

U.S. Pat. No. 7,064,893 Boutet et al.

The variable-transparency optical elements all receive the light from source 22 and are able to constitute light sources equivalent to the light sources of FIG. 1A.

To accomplish this, in the case of the device of FIG. 1B, control means 11 of FIG. 1A are replaced by control means 26, which are designed to control the illumination of source 22, and to make in sequence firstly transparent and then opaque the optical elements of the matrix, by synchronising the transparency-opacity of each element with the measurement of the corresponding light, made by photodetector 10.

For example, in the case of FIG. 1B, matrix 24 is controlled in such a way as to make all its elements opaque except for element $24_2$, which then allows the light of source 22 to pass to corresponding dot $14_2$, and thus constitutes (in association with source 22) a source equivalent to source $2_2$ of FIG. 1A.

Let us return to this FIG. 1A. The light originating from the light sources is, if necessary, optically shaped using appropriate optical components (not represented), for example lenses, filters or optical fibres.

After having traversed a dot, for example dot $14_2$, which is positioned facing an illuminated source, for example source $2_2$, the light reaches corresponding scatterer $12_2$, positioned on the surface of plate 4. A fraction of the light coupled due to this scatterer $12_2$ is then propagated in plate 4 by total reflection, and emerges from the latter through its edge, or more specifically through the sides of the plate, as can be seen in FIG. 1A.

"Positioned on the surface of the plate" is understood to mean that the scatterer is positioned in contact with the plate, or at a distance from the latter which is less than the wavelength emitted by the source (or less than the maximum wavelength when the illumination produced by the source is not monochromatic).

Photodetector 10 is positioned in front of one 28 of the sides of the plate, and gives an electrical signal representing the luminous flux reaching it, to appropriate electronic processing means (not represented).

An optical system (not represented) to shape the light rays which emerge from plate 4 can be positioned between output side 28 and photodetector 10. This system consists for example of lenses, filters or optical fibres.

Photodetector 10 can include a single photosensitive element, or photosite (for example, a phototransistor or a photoresistor or a photomultiplier), or include a matrix of photosites (for example, a pixilated image sensor or a strip of photodiodes), or can even be constituted by a spectrophotometer.

If a matrix of photosites is used, this can be made equivalent to a single photosite, by summing the signals produced by all the photosites, either in a subsequent stage by means of a software or electrical procedure, or at the photodetector itself (binning technique). It is also possible to use the photosites matrix to make a spectral measurement.

In the example of FIG. 1A, circulation chamber 16 is closed, on the side opposite the light sources of the device, by an opaque wall. On the other side the chamber is closed by transparent plate 4. Transparent optical windows, such as windows $30_1$, $30_2$, $30_3$, are then provided in the opaque wall, respectively opposite the light sources.

Figure 2:
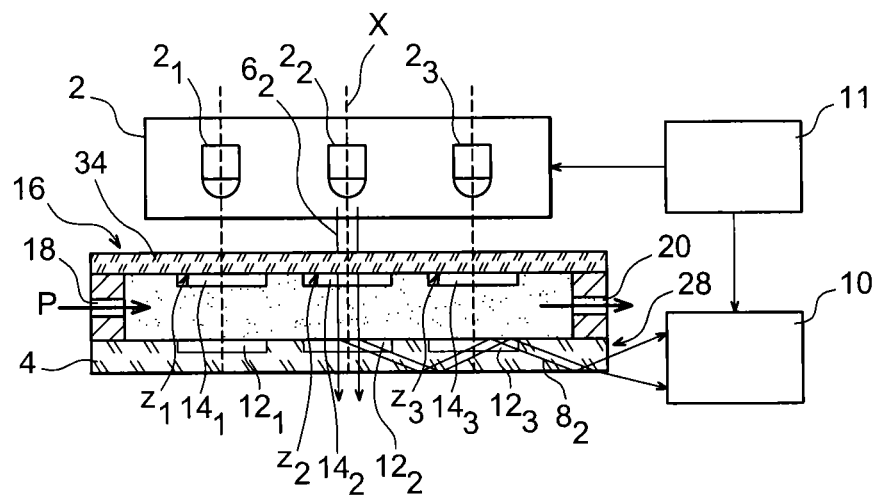
FIG. 2 is a schematic section view of another particular embodiment, in which the dots and the coupling elements are positioned on two different support plates.

As a variant, the circulation chamber can be closed by two transparent plates. In the example of FIG. 2, one of these plates is plate 4, as before; and the other plate 34 is facing the sources, and thus replaces the opaque wall mentioned above.

In the example of FIG. 1A, the dots are positioned directly on the light scatterers.

In another example, illustrated schematically by FIG. 2, the dots are positioned on a first transparent support which consists of a transparent plate 34 in the represented example, whereas the scatterers are positioned on a second transparent support, namely plate 4 (constituting the light guide).

Figure 3:
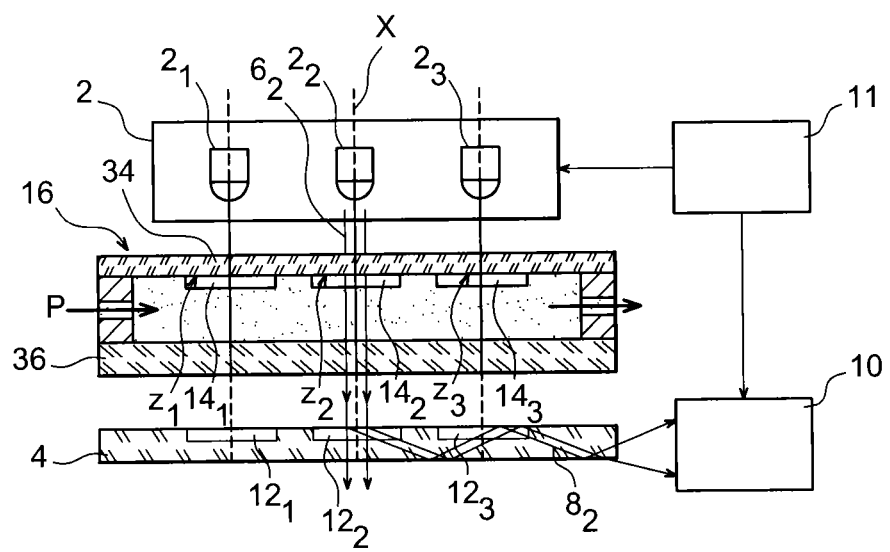
FIG. 3 is a schematic section view of another particular embodiment, which uses a circulation chamber, and in which the coupling elements are not manufactured in this chamber.

In another example of the invention, illustrated schematically by FIG. 3, the scatterers are always positioned on plate 4 (constituting the light guide), but the latter is dissociated from circulation chamber 16 in which the dots are located.

As can be seen in FIG. 3, the circulation chamber is delimited by transparent plate 34 and by another transparent plate 36; and plate 4, containing the scatterers, is positioned opposite this plate 36, outside the circulation chamber.

This embodiment enables assembly 12 of the scatterers to be installed permanently.

Circulation chamber 16 is designed in accordance with the product which it is desired to analyse. In certain cases a portion P of this product (in the liquid or gaseous form) is placed in this chamber, as is shown by FIGS. 1A, 1B and 2, and can react with the dots placed on the interrogation zones.

It is also possible to analyse several different products with a single device in accordance with the invention. The example represented schematically in FIG. 4 illustrates this possibility.

In this example, an assembly 38 of pits is used, for example of the microtiter plate type. Only pits $38_1$, $38_2$, $38_3$ are represented.

All the pits (the respective bases of which are transparent) are positioned on plate 4 (constituting the light guide) and therefore opposite assembly 2 of the light sources.

Figure 4:
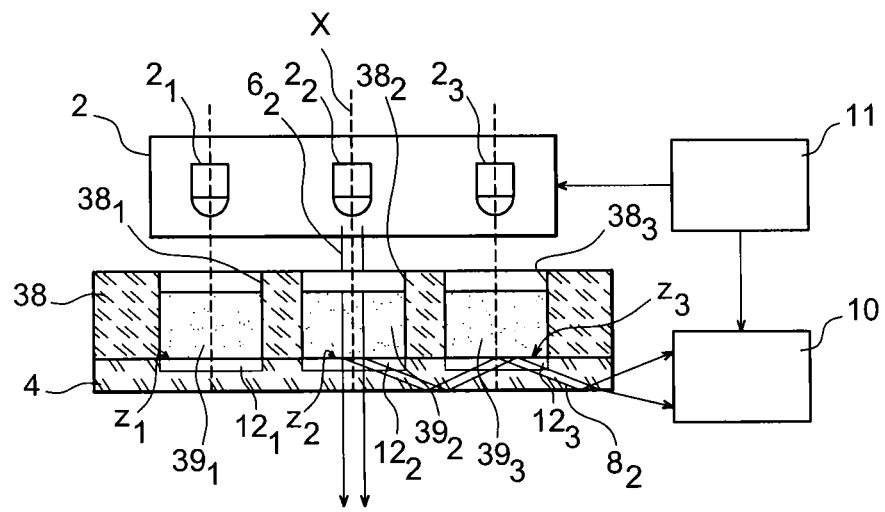
FIG. 4 is a schematic section view of another particular embodiment, in which the materials are positioned in pits.

The relative sizes and positions of the pits are such that each pit is facing a scatterer, as can be seen in FIG. 4.

The products, in liquid or solid form, or in the form of porous films or sol-gel, are positioned in the pits in which the sensitive materials (not represented) have previously been positioned. The reactions between the products and the sensitive materials then take place. A set of samples such as samples $39_1$, $39_2$, $39_3$ is thus obtained. The samples are analysed as explained above. Thus, according to this embodiment, a dot is formed by the product held in a pit.

As a variant, the reactions between the products and the sensitive materials can take place before the latter are introduced into the pits. The samples resulting from the reactions are then placed in the pits and the analysis is undertaken.

Figure 5:
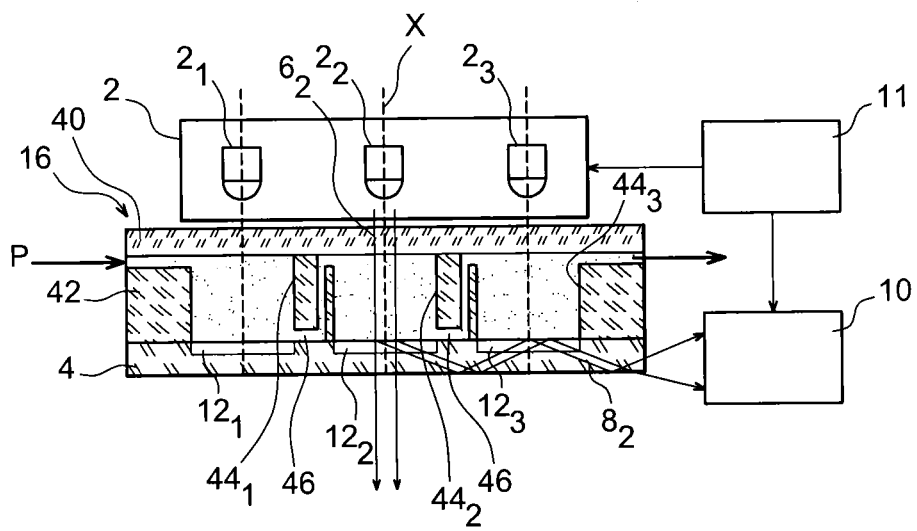
FIG. 5 is a schematic section view of another particular embodiment, using pits which communicate by feed-throughs.

Another example of the invention is illustrated schematically by FIG. 5.

In this other example a circulation chamber 16 is manufactured in which a portion of product P which it is desired to analyse is forced to flow, for example by means of a pump (not represented) or under the effect of vacuum. The circulation chamber is designed such that if there is no fluid actuation the product no longer flows, and such that the diffusion of the molecules that this product comprises is as small as possible.

As can be seen in FIG. 5, circulation chamber 16 is delimited by a transparent plate 40 and by plate 4 (constituting the light guide). Plate 40 is located on the side of assembly 2 of the light sources.

Between plate 40 and plate 4 there is a plate 42 in which an assembly of pits is formed (the respective bases of which are transparent), of which only pits $44_1$, $44_2$, $44_3$ are represented.

The pits of this assembly contain respectively the sensitive materials (not represented). In addition, the sizes and positionings of the pits are such that each pit is above a coupling element.

As in the embodiment represented in FIG. 4, each pit delimits a dot, where the dot is formed by product P when it fills the pit.

The change of quantity of product P from one pit to the next is made possible by means of feed-throughs such as feed-throughs 46, made between the pits. These feed-throughs are designed to allow the product to flow, when it is moved by a fluid actuator (using, for example, a vacuum or a pump), and to reduce the diffusion of the molecules of the product from one pit to the next when the actuator is stopped.

In what follows the scatterers are re-examined.

In the invention, in order to couple the light which has interacted with a sample, a scatterer is used which modifies the trajectory of the light rays because these rays are refracted. Of the latter, some are deflected within plate 4, with angles of incidence such that these rays are propagated by total reflection in the plate and emerge through the edge of the latter, allowing optical measurement by means of an appropriate photodetector.

Figure 6:
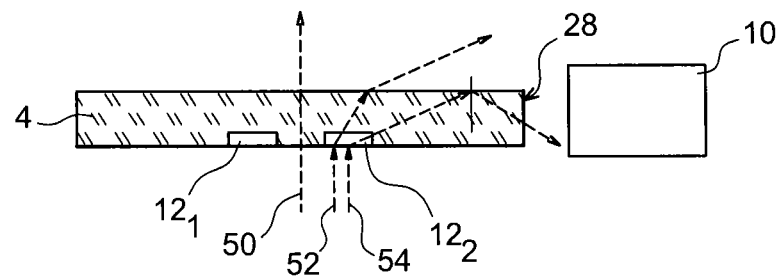
FIG. 6 illustrates schematically the principle of the deflection of the light rays by a scatterer which can be used in the invention.

FIG. 6 illustrates schematically the principle of the deflection of the light rays by a scatterer.

Plate 4, with scatterers such as scatterers $12_1$, $12_2$, can be seen.

Light ray 50 encounters no scatterer and its direction is not modified; it traverses plate 4, exiting through the face opposite the entry face.

Light ray 52 encounters scatterer $12_2$, but its refraction is insufficient for its angle to be greater, after the entry face, than limit-angle of total reflection $\theta_C$. Thus, light ray 52 also traverses plate 4, exiting through the face opposite the entry face.

It should be recalled that angle $\theta_C$ is defined by the following formula:

$$\theta_C = \arcsin(n_2/n_1) \tag{1}$$

where $n_1$ designates the refractive index of the plate and $n_2$ the refractive index of the medium in which this plate is placed.

Light ray 54 encounters scatterer $12_2$ and its refraction is sufficient for its angle to be greater, after the entry face, than limit-angle of total reflection $\theta_C$. This ray 54 is coupled in plate 4 and emerges through one 28 of its sides. It is then captured by photodetector 10 which is positioned facing this side 28.

In the present invention the measurement can be made by two complementary techniques, of scattering of light by a thick dot.

The first technique consists in measuring a reduction of the quality of light transmitted to photodetector 10 when the scattering of the light in the dot increases.

The second technique consists, on the contrary, in measuring an increase of this quantity of light falling on photodetector 10 when the scattering of the light in the dot increases.

Figure 7A:
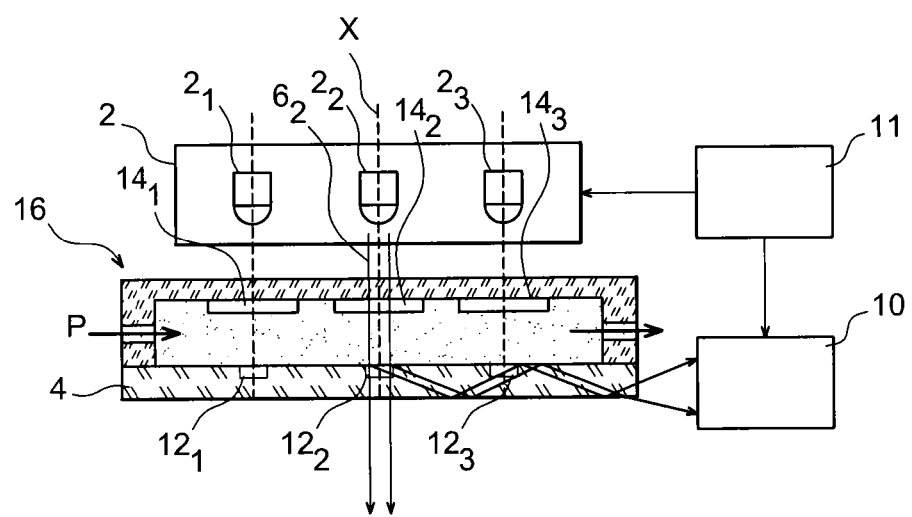
FIGS. 7A and 7B illustrate schematically a configuration which can be used in the invention, and which enables the light diffusion to be measured by diminution of the quantity of light reaching a photodetector.
Figure 7B:
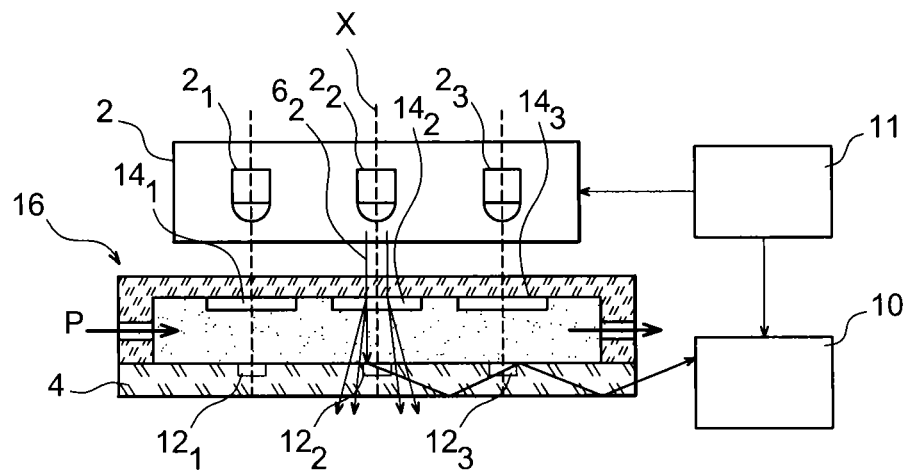

The first technique is illustrated schematically by FIGS. 7A and 7B (using a configuration of the type illustrated in FIG. 2).

In these FIGS. 7A and 7B, each scatterer, such as scatterer $12_2$, is manufactured to have an area less than or equal to the area of the cross-section of light beam $6_2$ arriving at this scatterer.

If dot $14_2$ located in the associated interrogation zone does not scatter, all the light traversing this dot arrives at scatterer $12_2$ and a first level of light is measured by photodetector 10 (FIG. 7A).

Conversely, if dot $14_2$ scatters, the light is deflected and a lesser quantity of light arrives at scatterer $12_2$. A second level of light is then measured which is lower than the first level (FIG. 7B).

Figure 8A:
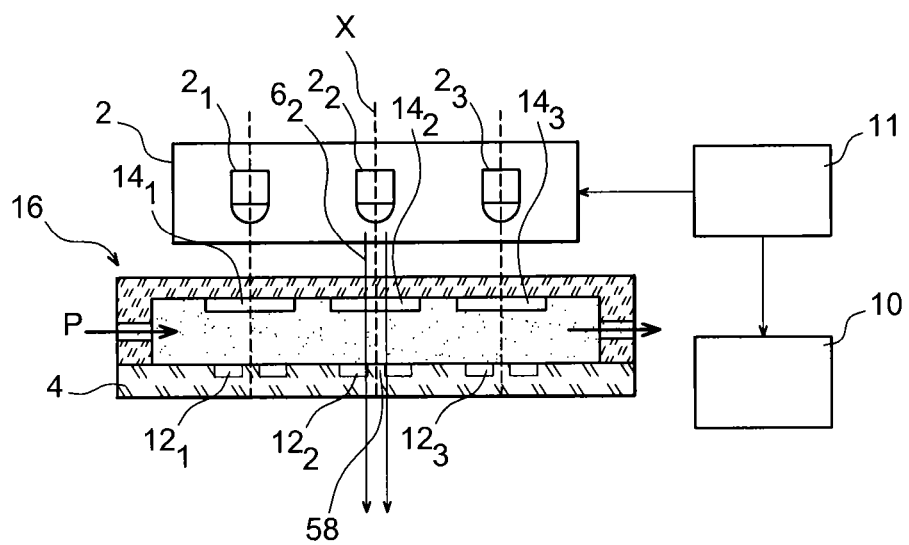
FIGS. 8A and 8B illustrate schematically another configuration which can be used in the invention, and which enables the light diffusion to be measured by increase of the quantity of light reaching the photodetector.
Figure 8B:
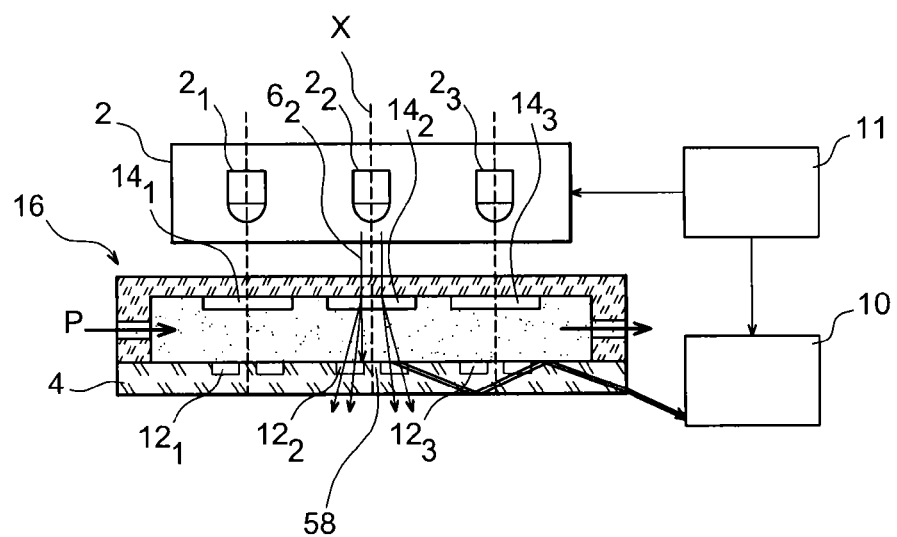

The second technique is illustrated schematically by FIGS. 8A and 8B (also using a configuration of the type illustrated by FIG. 2).

In these FIGS. 8A and 8B, each scatterer, such as scatterer $12_2$, is manufactured such that it is in the shape of a (scattering) ring which surrounds, or delimits, a central zone 58 of plate 4 (having the scatterers); and this central zone 58, for its part, does not constitute a scatterer.

In addition, each scatterer, such as scatterer $12_2$, is shaped such that the area of the disk it delimits is greater than or equal to the area of light beam $6_2$ arriving at this scatterer.

If dot $14_2$ located in the associated interrogation zone does not scatter, all the light traversing it arrives at central zone 58 of the scatterer, and a first level of light is measured (FIG. 8A).

Conversely, if scatterer $14_2$ scatters, the light is deflected and a proportion of this light reaches ring 58 which allows the light to penetrate into plate 4. A second level of light is then measured which is higher than the first level (FIG. 8B).

In the invention, the scatterers used are preferably constituted by surface rough zones, formed on the surface of the light guide, and therefore form scattering surfaces.

The shape and geometrical parameters of each scattering surface are defined firstly according to the directivity of the associated light source and, secondly, according to the quantity of coupled light required to make a precise reference measurement.

The device forming the object of the invention is also based on the association of each interrogation zone with a separate scatterer.

If a scatterer were to be used which was formed over the entire plate constituting the light guide, the phenomenon of total internal reflection, which lies behind the guiding of light, would be greatly attenuated, and the device would no longer be able to operate correctly since the light would be decoupled as it was propagated.

The area of a scatterer may typically be between 0.5 and 10 times the area formed by the dot on the plate, and preferably between 0.5 and 5 times this area.

The quantity of light which is coupled due to a scattering surface is also dependent on the roughness of this surface. This roughness, which is expressed as the arithmetic roughness, noted Ra, depends on the technique used to manufacture the scattering surface.

The roughness of a glass surface, of the microscope plate type, is approximately equal to 2 nm; it is very much less than the wavelengths of the light which can be used in the invention to illuminate the samples; and such a surface does not scatter sufficient light for the measurements to be usable.

For example, in the visible field, with a wavelength $\lambda$ of 500 nm, a roughness Ra of 2 nm, and glass plate made of borosilicate, having a refractive index $n_1$ equal to 1.523 and placed in air (the refractive index $n_2$ of which is equal to 1), it is found that total coupled intensity $I_c$ in the plate is equal to 0.01% of intensity $I_o$ of the incident light. On this subject, reference will be made to the following document:

J. M. Elson et al., "Relationship of the total integrated scattering from multilayercoated optics to angle of incidence, polarization, correlation-length, and roughness crosscorrelation properties", Appl. Opt., 22, 3207 (1983).

To determine $I_c$ the following formulae are used:

$$R = \left[\frac{n_1 - n_2}{n_1 + n_2}\right]^2 = 0.04 \qquad (2)$$

$$D = R\left[\frac{4\pi Ra}{\lambda}\right]^2 \approx 10^{-4} \qquad (3)$$

$$I_C = D \times I_0 \qquad (4)$$

where R designates the reflection factor and D the scattering factor.

In the present invention the surface is therefore made scattering by increasing roughness Ra, according to the desired value, by various techniques which are described below.

Roughness Ra, used in the invention, is greater than the wavelengths of the light which can be used to illuminate the dots. But in order to be effective it is preferable that this roughness Ra should be between 100 nm and 50 μm, values for which equation (3) is in fact no longer valid. In other words, the roughness must be, preferably, between one tenth of the wavelength and 100 times the wavelength (or average wavelength) emitted by the source.

Figure 9A:
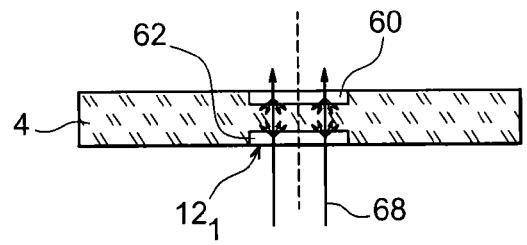
FIGS. 9A and 9B illustrate schematically two examples of scatterers which can be used in the invention, namely a scatterer consisting of two symmetrical portions (FIG. 9A) and a scatterer consisting of two asymmetrical portions, manufactured so as to face one another (FIG. 9B)
Figure 9B:
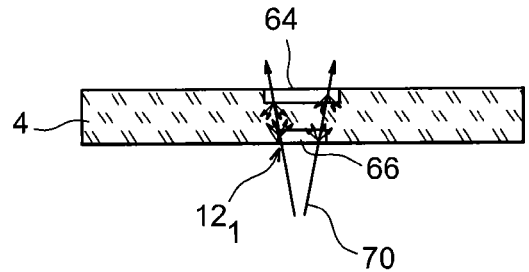

On the other hand, in order to increase further the quantity of coupled light, it is possible to manufacture two scattering surfaces which face one another, and which are either symmetrical (FIG. 9A), or asymmetrical (FIG. 9B).

More specifically, in the example of the invention which is schematically and partially illustrated by FIG. 9A, each scatterer, such as scatterer $12_1$, is in two portions 60, 62 having the same size, positioned opposite one another, on two opposite faces of plate 4 constituting the light guide.

And, in the example of the invention which is schematically and partially illustrated by FIG. 9B, each scatterer, such as scatterer $12_1$, is in two portions 64, 66 having different sizes, positioned opposite one another, on two opposite faces of slide 4.

The choice between these two possibilities is made in accordance with the expected results, the type of source used for the illumination and the shaping of the corresponding light beam.

For example, the configuration of FIG. 9A is well-suited to the case in which incident light beam 68 is collimated; whereas the configuration of FIG. 9B is applicable to the case in which incident light beam 70 is divergent.

There are many methods to create a scattering surface from a smooth surface.

This smooth surface can be frosted by a chemical attack, for example using hydrofluoric acid, ammonium bi-fluoride or hydrochloric acid. The actions of these acids can be localised, by deposing, on the plate the surface of which it is desired to frost, drops of such acids at the locations where it is desired to create frosted zones.

Milling using a diamond milling-cutter also enables a scattering surface to be obtained, as does erosion by ultrasound, using a tool the shape of which matches the sought pattern.

It is also possible to frost the surface by using a liquid, containing particles in suspension, and a tool of appropriate shape.

It is also possible to subject the surface to glass-blasting, after having protected the portions of it which it is desired not to frost.

An example of this latter method is described below.

A mask is firstly made to protect the regions which it is desired not to frost. This mask can be made using an adhesive film (for example of the Arcare 90106 type, sold by the Adhesive Research company) which will be removed after the glass-blasting. Cutting can be accomplished with a specialised robot (for example of the Craft Robo Pro E5000 type, sold by the Graphtec company).

The mask is then positioned on the glass plate. The glass-blasting may be accomplished with an industrial sand blaster and small glass beads. The diameter of the beads and the projection conditions (pressure of the sand jet, exposure time) define the roughness which will be obtained for the surface. After the projection the mask is removed and the plate is cleaned using an appropriate solvent, for example ethanol, acetone or isopropanol.

Scattering, transparent films can also be made to adhere to the zones of the surface where it is desired to form the scatterers, for example films made from a polyester such as polyethylene terephthalate or PET, which are semi-transparent and milky.

Many scatterers, developed for lighting, are also commercially available.

It is also possible to obtain a deflection of the light rays in the chosen regions of the support through the use of micro-prisms or Fresnel lenses, manufactured by embossing in these regions, for a support consisting of a transparent plate which is made from a synthetic material such as PMMA or polystyrene.

As a variant, a film including micro-prisms and a Fresnel lens structure can be made to adhere to the support. Many products of this type, developed for lighting, are commercially available.

In what follows an example of use of the invention is given.

Figure 10A:
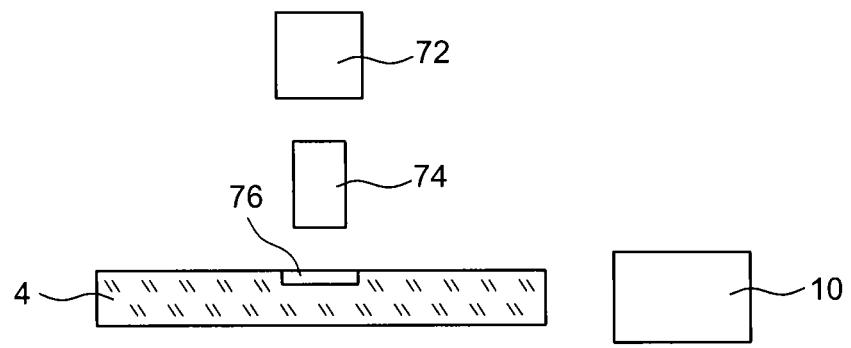
FIGS. 10A and 10B are schematic views of measuring devices.

A measuring device which is very schematically represented in FIG. 10A is used.

A light source 72 illuminates a pit 74 formed by a transparent bulb filled with Cooper eosin, placed (a few millimeters) above a microscopic plate acting as a multi-mode light guide 4. The eosin filling the transparent bulb therefore constitutes the dot.

Light source 72 is constituted by the end of optical fibres (optical fibre bundle, of diameter 6 mm), the other end of which is coupled to a halogen lamp (Volpi Intralux 6000).

Light guide 4 is a microscope plate of area 25 mm×75 mm, and 1 mm thick. This light guide includes, on one surface facing the eosin bulb, a scatterer 76 produced by sand-blasting according to a disk of diameter 4 mm. In other words, in this case the scatterer is a frosted glass disk formed at the surface of plate 4.

Figure 11:
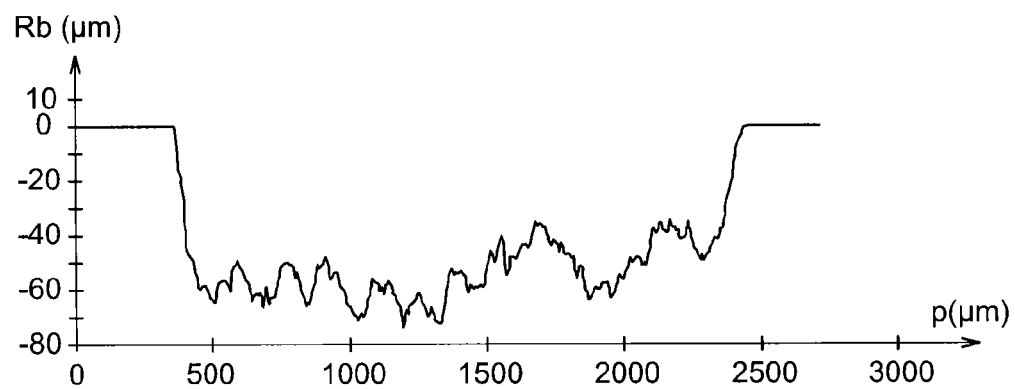
FIG. 11 represents the profile of a frosted surface of a glass plate, where this profile corresponds to the results of a measurement made using a profilometer (in µm) according to the position along the surface (in µm)

FIG. 11 represents a roughness profile of this frosted scatterer, produced with a KLA profilometer (Tencor) connected to a stylus forming a tip with a 60° angle at the top, the end of which is rounded (radius 2 µm). The profile is obtained by sweeping 2704 points 1.99 µm apart, at a speed of 100 µm/s, applying a force of 2 mg.

In the abscissa position p (in µm) has been shown, and in the ordinate the crude roughness has been shown (in µm). In FIG. 11, the position of the scatterer approximately corresponds to the 400 µm to 2400 µm abscissae.

Photodetector 10 consists of a polymer optical fibre, connected to a spectrophotometer (Ocean Optics QE65000).

This photodetector 10 is placed opposite the edge of the glass plate, and the spectrum of the light deflected by the scatterer and propagated as far as the edge of light guide 4 is measured.

Figure 10B:
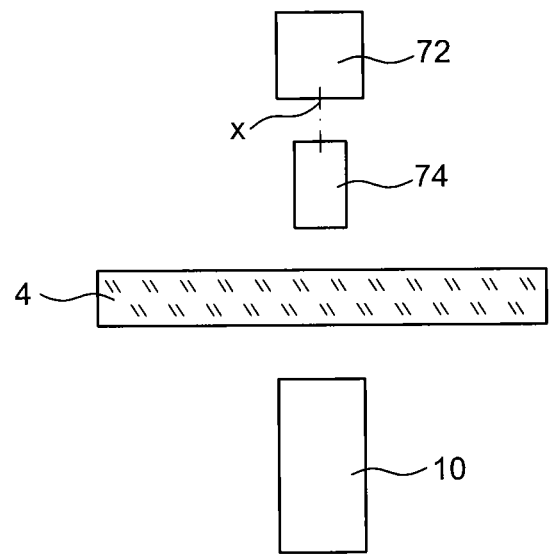

In another measurement the assembly represented very schematically in FIG. 10B is used.

The equipment used is similar to that of the previous example, except for light guide 4, which is shaped like a microscope plate comparable to the previous one, except that it has no scatterer.

In this assembly, as can be seen, photodetector 10 is positioned opposite illumination axis x of light source 72. The spectrum of the light radiation transmitted by the eosin, and by the thickness of the glass plate, is thus obtained, without scattering.

Figure 12:
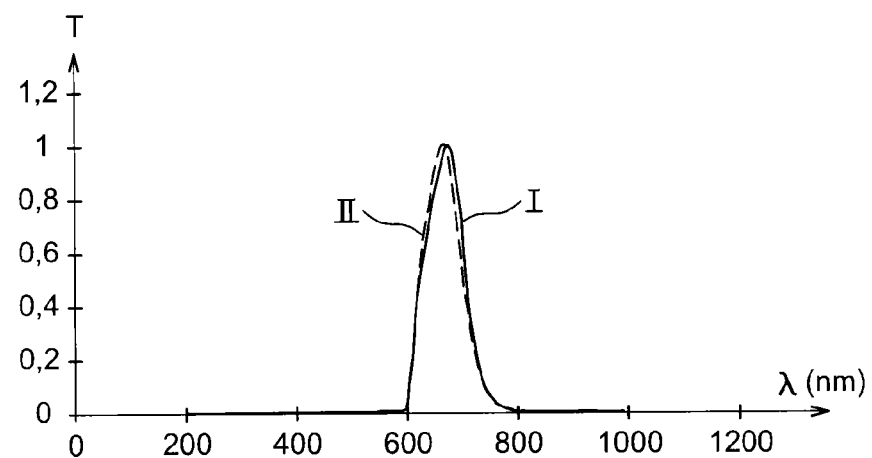
FIG. 12 represents two transmission spectra according to the wavelength (in nm) of the light transmitted by a dot.

The wavelength spectra produced are represented in FIG. 12.

These are spectra which have been normalised relative to their maximum intensity signal. In the abscissae wavelength λ (in nm) has been included, and in the ordinates transmission T has been included.

It can be seen that the deflection by the scatterer (device of FIG. 10A), corresponding to curve I of FIG. 12, does not modify the spectrum of the light transmitted by the dot (device of FIG. 10B), corresponding to curve II of FIG. 12.

The invention claimed is:

1. A device for optical measurement of a material, comprising:
   a transparent support, including at least one zone, where said zone is configured to be positioned opposite a dot including a material,
   a light source associated with said zone, where the light source is designed to emit light along an axis (X), in the direction of the zone with which the light source is associated, where the material of the dot interacts with the light received from said light source, and
   a light guide to convey a proportion of the light emitted by the dot, under the effect of illumination by the light source,
   wherein the light guide includes a light scatterer associated with said light source, where said scatterer is configured to cause a proportion of the light emitted by the dot to penetrate into said light guide, such that the light is guided in a direction perpendicular to the axis of the light emitted by said light source, wherein the scatterer has an annular shape, and thus delimits a zone of the light guide, and wherein the area of the zone is greater than or equal to the area of the cross-section of the portion of the light beam incident to the material.

2. A device according to claim 1, in which the light guide is multi-mode.

3. A device according to claim 1, including a plurality of dots.

4. A device according to claim 1, also including a photodetector to detect the light conveyed by the light guide, where said photodetector is positioned opposite an edge of the light guide.

5. A device according to claim 1, in which the thickness of the light guide is in a range of 50 µm to 10 mm, and preferably of 500 µm to 5 mm.

6. A device according to claim 1, in which the scatterer is positioned, at least partly, on the face of the light guide closest to the material.

7. A device according to claim 1, in which the scatterer includes a surface rough zone of the light guide, the arithmetic roughness of which is in a range of 100 µm to 50 µm.

8. A device according to claim 1, in which a multi-mode light guide constitutes the transparent support and thus includes the zone intended to receive the dot, where said zone is positioned opposite the scatterer.

9. A device according to claim 1, including a main light source and at least one optical element of variable transparency which is able to receive the light from the main light source and then to constitute the light source.

10. A device according to claim 1, including a plurality of materials intended to be illuminated in succession, by a light source, where each material is then associated with a scatterer which enables the light emitted by the material under the effect of the illumination by the source to be deflected in the light guide.

11. A device according to claim 1, including a plurality of materials and also a set of pits configured respectively to receive the materials, where each pit is positioned opposite a scatterer.

12. A device according to claim 1, wherein the material is one of a plurality of materials that are illuminated in succession, by the light source, each of the plurality of materials being associated with the light scatterer, the light scatterer enabling the light emitted by each of the plurality of materials, when illuminated by the light source, to be deflected in the light guide.

* * * * *